US008753120B2

(12) United States Patent
Pitel

(10) Patent No.: US 8,753,120 B2
(45) Date of Patent: Jun. 17, 2014

(54) ENDODONTIC PROCEDURE USING SELF-ADHESIVE RESIN CEMENTS AND SEALERS OR SELF ETCHING ADHESIVES AND CHEMICALLY BONDABLE OBTURATORS

(75) Inventor: Mark Pitel, Danbury, CT (US)

(73) Assignee: Heraeus Kulzer GmbH, Hanau (DE)

( * ) Notice: Subject to any disclaimer, the term of this patent is extended or adjusted under 35 U.S.C. 154(b) by 290 days.

(21) Appl. No.: 11/380,030

(22) Filed: Apr. 25, 2006

(65) Prior Publication Data

US 2007/0207445 A1    Sep. 6, 2007

Related U.S. Application Data

(60) Provisional application No. 60/779,682, filed on Mar. 6, 2006.

(51) Int. Cl.
*A61C 5/02*    (2006.01)

(52) U.S. Cl.
USPC .......................................... 433/224

(58) Field of Classification Search
USPC .......................................... 433/224, 102, 81
See application file for complete search history.

(56) References Cited

U.S. PATENT DOCUMENTS

| | | | | |
|---|---|---|---|---|
| 4,820,306 A * | 4/1989 | Gorman et al. | ............... | 128/898 |
| 5,658,149 A * | 8/1997 | Munce | .......................... | 433/224 |
| 5,883,153 A * | 3/1999 | Roberts et al. | ................ | 523/116 |
| 6,644,972 B1 * | 11/2003 | Mays | ............................. | 433/224 |
| 6,797,767 B2 * | 9/2004 | Stannard et al. | .............. | 524/559 |
| 6,953,535 B2 * | 10/2005 | Hecht et al. | .............. | 252/183.13 |
| 7,204,875 B2 * | 4/2007 | Jia et al. | .......................... | 106/35 |
| 7,211,136 B2 * | 5/2007 | Jia et al. | .......................... | 106/35 |
| 2002/0019456 A1 * | 2/2002 | Jia | ................................. | 523/115 |
| 2004/0137404 A1 * | 7/2004 | Koch et al. | ...................... | 433/81 |
| 2004/0202986 A1 * | 10/2004 | Haschke | ....................... | 433/224 |
| 2005/0066854 A1 * | 3/2005 | Jia | .................................. | 106/35 |
| 2005/0069836 A1 * | 3/2005 | Jia et al. | .......................... | 433/81 |

(Continued)

FOREIGN PATENT DOCUMENTS

WO    2006 022747    3/2006

OTHER PUBLICATIONS

"Healthy Teeth and Gums" http://healthyteeth.blogsome.com/2006/01/19/.*

(Continued)

*Primary Examiner* — Sunil K Singh
(74) *Attorney, Agent, or Firm* — Norris McLaughlin & Marcus, P.A.

(57) ABSTRACT

A method of filling and sealing a root canal during an endodontic procedure involves: a) filling the root canal with a combination of: i) an obturator composed at least in part of a chemically-bondable material; and ii) a self-etching adhesive or self-adhesive resin-based cement or sealer; and b) curing the combination to seal the root canal. Also disclosed is a kit for carrying out the method, the kit having as components: a) an obturator composed at least in part of a chemically-bondable material; and b) a self-adhesive resin-based cement or sealer.

12 Claims, 4 Drawing Sheets

(56) References Cited

U.S. PATENT DOCUMENTS

| | | | |
|---|---|---|---|
| 2006/0154212 A1* | 7/2006 | Koch et al. | 433/224 |
| 2006/0154213 A1* | 7/2006 | Koch et al. | 433/224 |
| 2006/0234190 A1* | 10/2006 | Koch et al. | 433/224 |
| 2007/0015106 A1* | 1/2007 | Bertl et al. | 433/80 |
| 2007/0065783 A1* | 3/2007 | Tuttle et al. | 433/224 |

OTHER PUBLICATIONS

Pinzon et al. The Dental Advisor. "In Vitro Bond Strenght of Adhesive Cements to Tooth Structure." Jun. 2005. http://multimedia.mmm.com/mws/mediawebserver.dyn?6666660Zjcf6IVs6EVs66S&HRCOrrrrQ-.*

Malcmacher, Louis. Dental Economics. "Do you endo?" Dec. 2005. http://rdh.pennnet.com/articles/article_display.cfm?article_id=243748.*

Kulzer, Heraeus. "InnoEndo" http://www.heraeus-kulzer-us.com/webcontent.omeco?DOCID=1343&PHPSESSID=653a8eb424c635451d70248e2306e142&PHPSESSID=bd6bca0e68d657461f26bab56892403f&PHPSESSID=b3f8ba73d998195db387e19338dd3de3&PHPSESSID=c0aa787e0b9f573866a684dcc4b7f477.*

* cited by examiner

The same lower case letters denotes no statistically significant difference in mean

ENDODONTIC PROCEDURE USING SELF-ADHESIVE RESIN CEMENTS AND SEALERS OR SELF ETCHING ADHESIVES AND CHEMICALLY BONDABLE OBTURATORS

BACKGROUND OF THE INVENTION

1. Field of the Invention

The present invention relates to the field of endodontics.

2. Description of Related Art

Root canal therapy has become well established as a viable clinical treatment to retain a tooth where the dental pulp has become painful, irreversibly inflamed, infected or necrotic (dead). The generally accepted method of performing a root canal is to drill an "access" opening into the root canal through the clinical crown of the tooth and then to remove the diseased or damaged pulpal tissues using small sharp files, rotary files, dental burs or drills. Once the pulpal tissue is removed, the root canal is treated with chemical agents to disinfect the canal, to remove any residual organic material and to remove what is commonly referred to as the debris "smear layer." The cleaned root canal must then be "obturated," which means that it is filled with an inert material that is capable of sealing the canal against the passage of fluids and microorganisms.

There are many strategies, materials and techniques that have successfully been used to obturate root canals. One method is simply to fill the root canal with an inert paste that is placed into the canal as a viscous liquid but sets hard after a period of working time. Historically, one of the most popular strategies is to use a solid core filler (sometimes called a "cone" or a "point") which is surrounded by a viscous liquid sealer or paste. Like the method described above, the sealer is what is really providing the seal, but the solid core filler is necessary to hydraulically force the sealer around curves, into the small irregularities and accessory canals coming off the main root canal. The solid core filler also offers a convenient pathway back to the apex of the root canal should retreatment ever become necessary. These solid core fillers can be flexible, semi-rigid or rigid. The benchmark or gold standard for obturation that has emerged and dominated endodontics over the past century is to use a solid core filling of "gutta percha" and a self-setting sealer based on a formula made with zinc oxide and eugenol. Gutta percha was first introduced into dentistry by Edwin Truman as filling material in 1847 and was called Hill's stopping. Due to its thermoplastic properties, it rapidly found its way into popular use in endodontics by 1887 in the form of gutta percha points. In spite of the overall acceptance and clinical success of the gutta percha/sealer cement combination, many clinical studies have shown that the combination still leaks and diminishes the efficacy of the root canal seal. This has led to the continual search for easier and better materials to seal the root canal.

U.S. patent application Publication No. 2005/0069836 describes a new type of polyester based, thermoplastic obturation material that is able to fulfill all of the same functions as gutta percha but which also takes advantage of a much stronger chemical adhesion/bonding strategy to improve the seal. A commercial product believed to be embraced by this patent application is RESILON™ (polycaprolactone-based thermoplastic aliphatic polyester resin obturation material). In other words, RESILON™ can be thought of as a soft thermoplastic resin that is chemically bondable. This differs from gutta percha, which is based upon a naturally occurring latex rubber and is not chemically bondable. So, instead of simply cementing the point into the root canal, it is now possible to adhesively bond the point in and achieve a superb water tight, insoluble seal throughout the length of the canal.

What makes RESILON™ so important is that it takes advantage of the important scientific discipline referred to as "Adhesion Dentistry" or "bonding." Bonding in dentistry has enjoyed explosive growth and improvement since its introduction. Through modern adhesion dentistry it is now possible to strongly link many different substrates to tooth structure, including resin composites, porcelains, and metals. However, RESILON™ marks the first real linking of endodontic obturation and adhesion bonding.

Adhesion bonding as well as the resin based restoratives in dentistry are almost all based upon compounds composed of monomeric precursors containing a C=C (carbon-carbon) double bond and which are catalyzed into linking and crosslinking into a solid, virtually insoluble polymeric structure. The composite resin restorative materials are generally highly filled with glass or silica particles to convert them into pastes, improve their strength and durability whereas the bonding agents are largely unfilled or sparsely filled, allowing them to remain as liquids. There are two main initiator systems used to convert the monomers into polymers. These are the photoinitiators and chemical initiators. This has allowed the creation of purely light cured resin composites and bonding agents (photoinitiated) as well as purely self/auto cure resin composites and bonding agents. There are also hybrid resin composites and adhesives which contain both initiator systems and are referred to as "dual cured." The attachment of these polymeric restorative and adhesive materials to tooth structure requires a special chemical treatment of the tooth surface called "etching." In the process of etching, a weak acid is applied to the tooth which extracts some of the calcium hydroxyapatite salts that mineralizes both enamel and dentin. The resultant surface is able to adhere to the adhesive products much more efficiently.

A number of manufacturers currently utilize RESILON™ in their root canal protocols. EPIPHANY™ and REALSEAL™ utilize solid core obturators made entirely of RESILON™. To bond these obturators into the canal, the dentist first irrigates the canal with NaOCl (sodium hypochlorite). This clears the canal of organic debris and disinfects. EDTA (ethylene diamine tetraacetic acid) is then used to neutralize the NaOCl and demineralize the walls of the root canal. This is followed by the placement of an adhesive primer and then the placement of a dual cured resin based endo sealer. The RESILON™ point is seated into the sealer and stabilized by light curing from the crown side. After a period of time, the self-curing/autocuring chemistry of the sealer will activate allowing the sealer deep in the canal to set fully. The result is a total adhesive seal from the apex of the root to the crown with a central core of RESILON™.

INNOENDO™ and SIMPLIFILL™ are carrier based obturators. SIMPLIFILL™ utilizes a metal rod carrier to push a small plug of RESILON™ deep into the canal. The carrier rod is then twisted and removed and the remaining space in the canal is backfilled with RESILON™ points. INNOENDO™ utilizes a fiberglass carrier which holds a small tip of RESILON™ on the end. As the INNOENDO™ is seated into the canal the RESILON™ is forced down deep into the canal all the way to the apex of the root. However, in INNOENDO™, the carrier is left in the root canal and forms the seal in the upper coronal part of the canal. Since all manufacturers are basically licensing the RESILON™ Technology from Resilon Research LLC, they all use the very same RESILON™ material and variations of the same resin based primers and sealers. So for INNOENDO™ and SIM- PLIFILL™ you are also required to irrigate the tooth with NaOCl and EDTA, followed by an adhesive primer and sealer application.

Progress has allowed the development of what have been described as "self-etching dental adhesives" and "self-adhesive resin composites." These products have an acidic formula that allows them to bond to tooth structure without the necessity of pretreating the tooth with a weak acid. This permits the dentist to save time during the clinical treatment. Most recently, there have been introduced into the marketplace several "self adhesive resin cement" products. These products allow for a much more reliable, higher strength adhesive bonding like attachment of dental restorations such as dental crowns and bridges, dental inlays and onlays and laminate veneers to tooth structure. Dentists like these products because they eliminate the extra etching step but can still maintain high bond strengths of resin bonding. Commercial examples of the self adhesive resin based cements include UNICEM™ (3M/ESPE), MAXCEM™ (Kerr Dental) and EMBRACE WETBOND™ (Pulpdent), the latter of which is believed embraced by U.S. Pat. No. 6,797,767.

Thus far, these "self-etching dental adhesives" and "self-adhesive resin composites" have not been used in endodontics, and particularly not as sealers for root canal obturations.

In spite of improvements resulting from the use of RESILON™, further improvements in seal strength and other properties are needed.

SUMMARY OF THE INVENTION

These and other objects were met with the present invention, which relates in a first embodiment to a method of filling and sealing a root canal during an endodontic procedure, wherein the method comprises:
  a) filling the root canal with a combination comprising:
    i) an obturator composed at least in part of a chemically-bondable material; and
    ii) a self-adhesive resin-based cement or sealer or a self etching adhesive; and
  b) curing the combination to seal the root canal.

In a second embodiment, the present invention relates to a kit for use in filling and sealing a root canal during an endodontic procedure, wherein the kit comprises:
  a) an obturator composed at least in part of a chemically-bondable material; and
  b) a self-adhesive resin-based cement or sealer or a self etching adhesive.

BRIEF DESCRIPTION OF THE DRAWINGS

The invention will now be described in greater detail with reference to the drawings, wherein.

DETAILED DESCRIPTION OF THE INVENTION

Endodontic failure can be due to a number of factors, including apical and/or coronal leakage, root fractures, insufficient disinfection and anachoresis. Prevention of leakage is especially important because endodontic treatment results in the loss or reduction of one's ability to feel/sense bacterial breakdown coronally. Percolation at the restoration margins may go unnoticed by the patient for long periods of time, and, thus, may be brought to the attention of the dentist too late to resolve the problem. Indeed, studies indicate that significant bacteria leakage following exposure of sealed root canals to artificial and natural saliva may occur in as little as two days post-procedure, leading to complete bacterial leakage. Accordingly, much energy has been expended in the art making certain that root canal sealing is as effective as possible.

Figure 1:
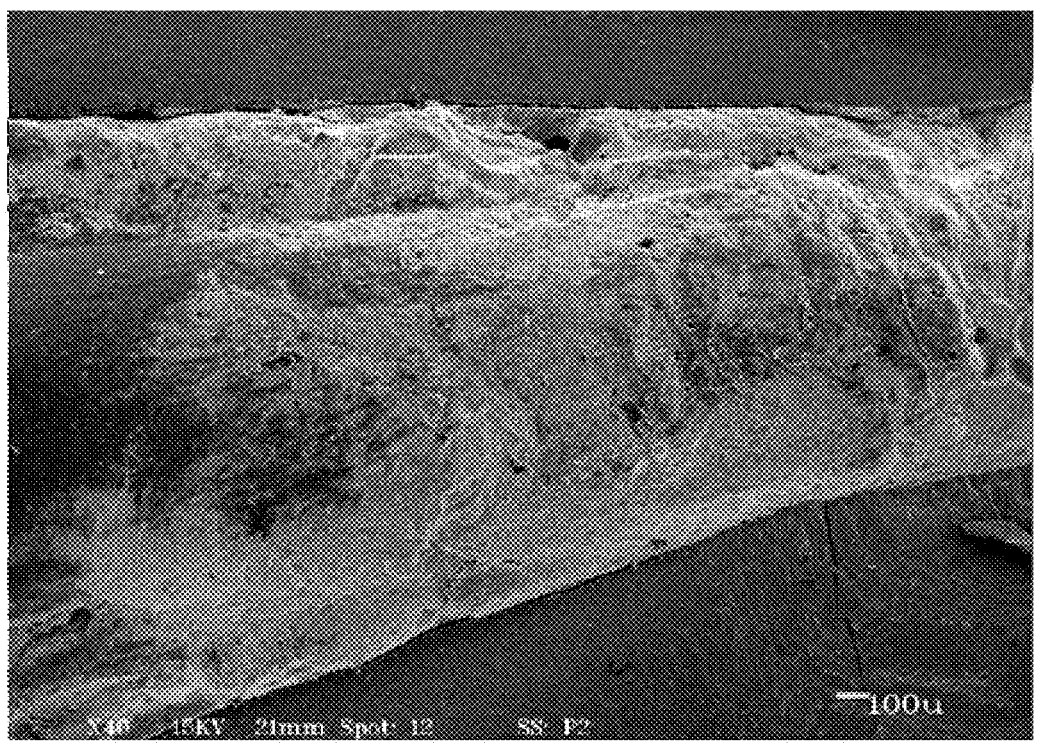
FIG. 1 is a micrograph of a root canal sealed with a gutta percha point and a conventional non-adhesive cement sealer.
Figure 2:
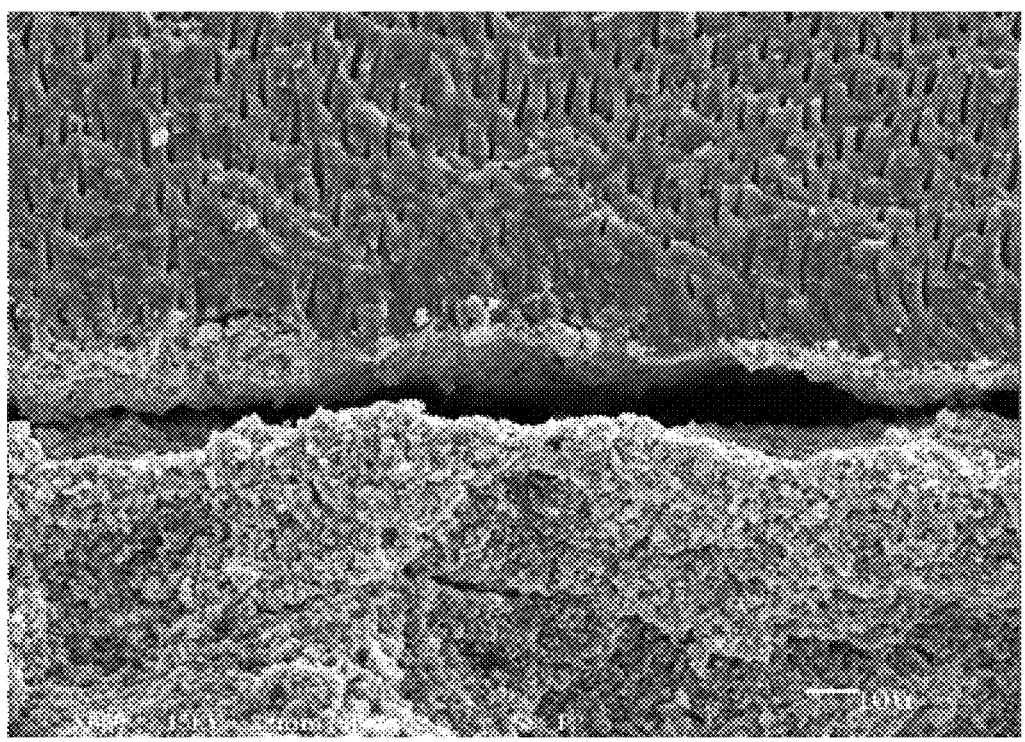
FIG. 2 is a micrograph of the root canal seal of FIG. 1 at 10× magnification.

Shown in FIG. 1 is a micrograph of a portion of a root canal sealed according to a known technique. FIG. 2 shows the same root canal, but at 10× magnification. It is seen in FIG. 2 that upon closer inspection there are gaps between the dentin and the sealant. These gaps can provide channels of egress for bacteria into the dentin and the tissue beyond, resulting ultimately in failure of the endodontics.

In an effort to provide a formidable seal, and at the same time simplify the procedure, it has been discovered that the use of self-adhesive resin cements and/or sealers in conjunction with the use of obturators composed at least in part of a chemically-bondable material provide superior seals, and may involve a more efficient sealing procedure.

Figure 3:
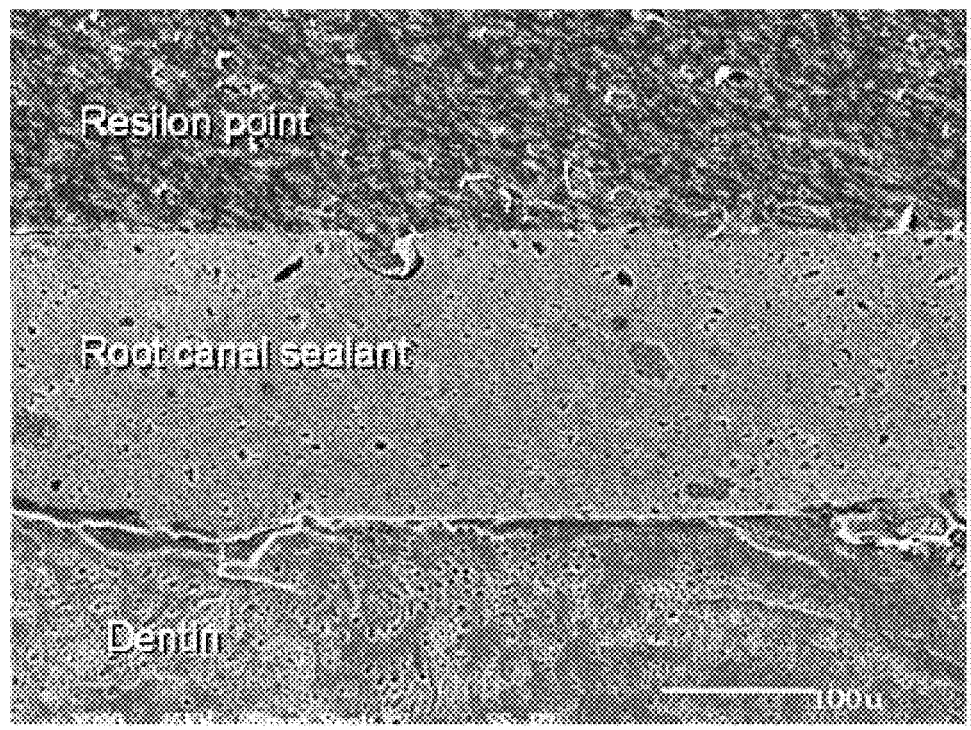
FIG. 3 is a micrograph of a root canal sealed according to an embodiment of the inventive protocol.
Figure 4:
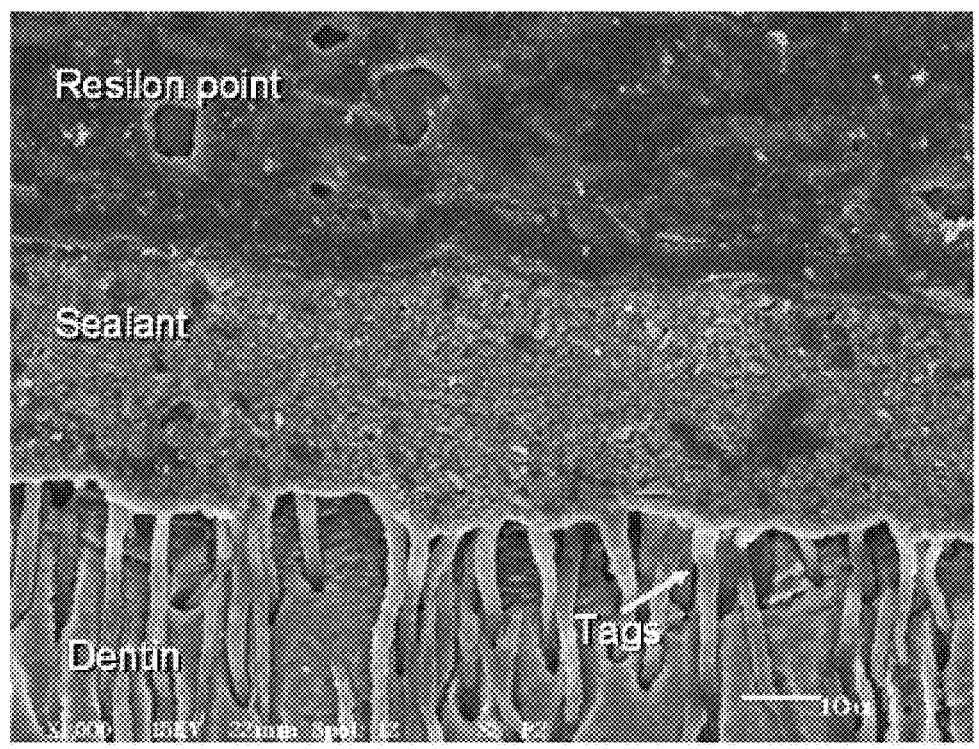
FIG. 4 is a micrograph of the root canal seal of FIG. 3 at 10× magnification.

FIG. 3 is a micrograph of a portion of a root canal sealed with a RESILON™ point and a self-adhesive sealant. FIG. 4 shows the same root canal, but at 10× magnification. It is seen in FIG. 4 that there are no gaps between either the sealant and the point or between the sealant and the dentin. In fact, the sealant bonds with the dentin to make an excellent adhesive seal, as evidenced by the projections, or "Tags," extending from the sealant deep into the dentin.

The idea is to achieve an excellent seal at every point where weakness might exist, for example, between the sealant and the obturator or between the sealant and the dentin, whether within the main root canal or within the accessory canals or irregularities. To that end, use is made of an obturator composed at least in part of a chemically-bondable material. The chemically-bondable material is any suitable such material. Preference is given to gutta percha which has been impregnated, coated or treated in any such a way as to render the gutta percha chemically-bondable; or a polymer-based, thermoplastic obturation material, such as RESILON™, for example, as described in US 2005/0069836, the entire contents of which are incorporated herein by reference; or a resin-modified glass ionomer. Especially preferred at this point is the RESILON™ material.

In one preferred embodiment, the obturator is composed only in part of the chemically-bondable material. In one particularly preferred embodiment, the obturator is composed in a first part of fiberglass and in a second part of the chemically-bondable material, such as, for example, the post and tapered fiberglass points available from INNOENDO™ (Heraeus Kulzer), which may be tipped with any of the foregoing chemically-bondable materials, especially the RESILON™ material.

In another preferred embodiment, the obturator is composed in whole of the chemically-bondable material. In this embodiment, the chemically-bondable material may, again, be any of the fore going chemically-bondable materials, especially the RESILON™ material.

The self-adhesive resin-based cement or sealer is any suitable such material. Preference is given to materials containing acid containing monomers, such as are described in U.S. Pat. No. 6,797,767, the entire contents of which are incorporated herein by reference. Due to the presence of the acid group, such materials can form excellent bonds to dentin themselves, without the need to use ethylene diamine tetraacetic acid (EDTA), and, thus, the customary irrigation step with EDTA can be dispensed with altogether if desired. Use of these materials also obviates the need to use the customary two-part adhesive primer, and, thus, this step can also be dispensed with altogether if desired. The result is a streamlined procedure that surprisingly provides as good, if not better, sealing than known procedures. Among the suitable cements and sealers, a preference is given to UNICEM™ (3M/ESPE), MAXCEM™ (Kerr Dental) and EMBRACE WETBOND™ (Pulpdent). Most preferred at this time is EMBRACE WETBOND™ (Pulpdent).

In a particularly advantageous embodiment, the self-adhesive cement or sealer will comprise a photoinitiator and/or a chemical initiator. Most preferred is a "dual cure" system comprising both a photoinitiator and a chemical initiator.

In an especially preferred embodiment, in an effort to simplify the steps involved in using adhesion endodontics, for example, with RESILON™, it was speculated that the self-adhesive resin cements might prove to be a suitable alternative to the primers and sealers provided by Pentron. In this way, it might be possible to eliminate the separate steps of applying an adhesive primer followed by an adhesive resin based dual cured sealer. As an example of a self-adhesive resin cement, EMBRACE WETBOND™ from Pulpdent was selected, and subjected to numerous studies where it was tested along side of the standard method. Results were rather striking. In every case the single step, self-adhesive cement used as an endodontic sealer outperformed every other combination of obturation materials and technique. Leakage was significantly reduced and the root was reinforced against fracture.

The invention will now be described in greater detail with reference to the following non-limiting examples:

EXAMPLES

Example 1

Tapered Point Obturator Seating

An access cavity is opened in the crown of a tooth to expose the root canal, and the pulp tissue is removed. An instrument is used to clean and shape the root canal to a predetermined working length. The root canal is irrigated with bleach to disinfect and dissolve residual pulp tissue. The root canal is irrigated with ethylene diamine tetraacetic acid (EDTA) to demineralize the surface of root dentin to remove the smear layer, although this step can be eliminated if desired. The root canal is dried thoroughly with paper points. Selection is then made of an appropriate size obturator. A rubber stop is fitted on the distal end of the obturator at the working length. The obturator is inserted into the root canal, and the proper seating is verified by radiograph, and then the obturator is removed temporarily.

A self-adhesive sealer is introduced into the root canal, for example, by spinning the sealer into the root canal with a lentulo filler instrument or a paper point. The selected obturator is placed into a disinfectant solution, and then seated into the root canal, and any excess sealer that extrudes from the root canal cleaned. The filling is light-cured with a standard curing light for 40 seconds. The portion of the obturator that protrudes from the crown is cut, and the coronal cavity is filled with, for example, INNOENDO™ dual cured or self cured core buildup material.

Example 2

Post Obturator Seating

The protocol of Example 1 is repeated except that after the root canal is irrigated with bleach to disinfect and dissolve residual pulp tissue (again only optional), the upper portion of the root canal may be drilled to widen the root canal to accommodate the post.

Example 3

Obturating Pellets by Method of Heat Extrusion

Analogous to Examples 1 and 2, the root canal may be obturated with the use of obturator pellets which have been heated in a suitable device to allow the liquefaction and extrusion of the obturating material into the root canal, for example, RESILON™ pellets.

Example 4

Dye Microleakage Study

Figure 5:
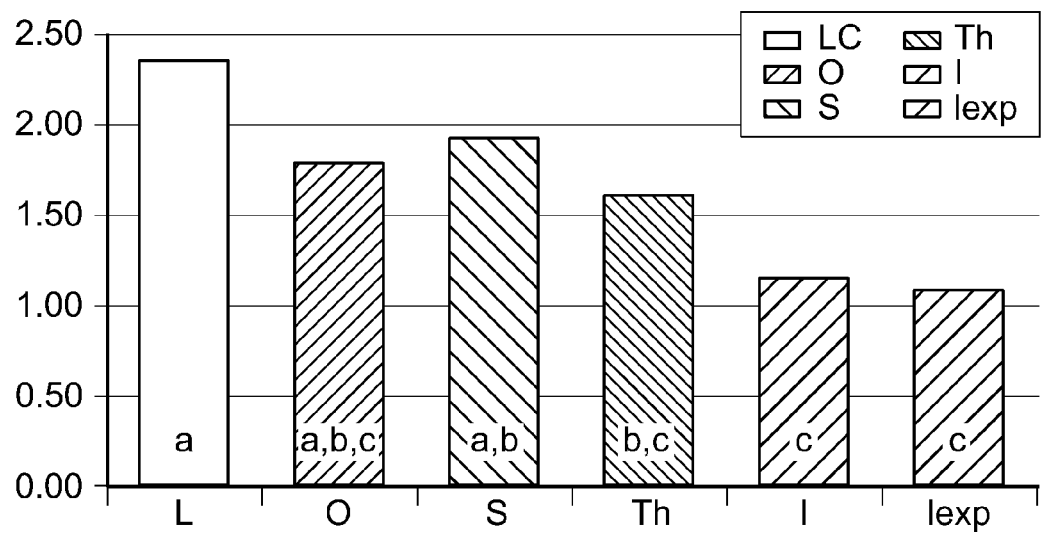
FIG. 5 is a chart comparing coronal dye leakage results among various manufacturers/protocols.
Figure 6:
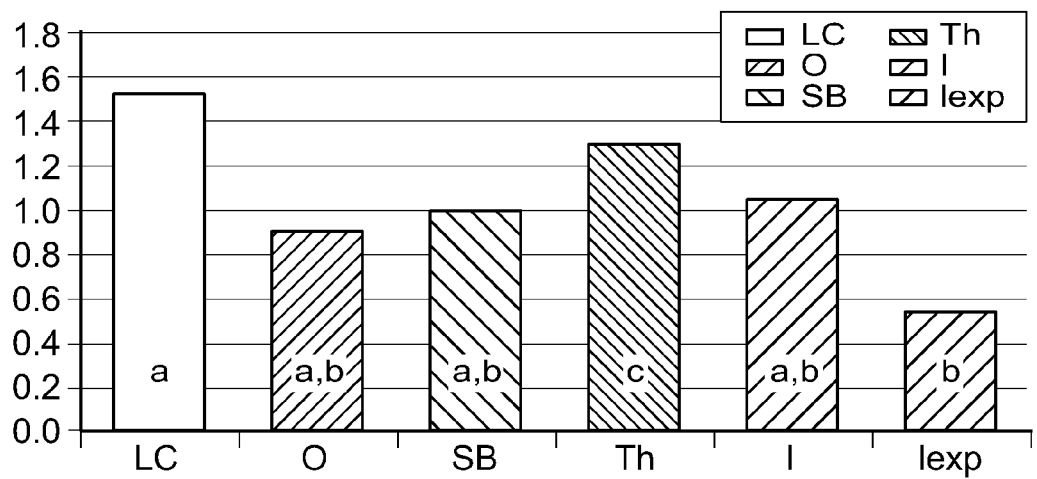
FIG. 6 is a chart comparing apical dye leakage results among various manufacturers/protocols.

Dye Microleakage was assessed from root canals sealed with various commercial products as follows:

Group 1: Control
Group 2: OBTURA II™ (Obtura Spartan)
Group 3: SYSTEM B™ (Kerr Sybron Endo)
Group 4: THERMAFIL™ (Tulsa Dental)
Group 5: INNOENDO™ (Heraeus-Kulzer)
Group 6: INNOENDO™ (Heraeus-Kulzer) using the inventive protocol The experimental protocol was follows: In each case, the root canal of an extracted tooth was sealed and obturated according to the manufacturer's directions or in the case of Group 6 as described herein. Each tooth was then stored in distilled water for 7 days at 37° C., and, thereafter, subjected to thermal cycling (1000 cycles, 5° C.-55° C.) in methylene blue dye. Each tooth was sectioned at 1 mm increments from the apical or coronal surface, and then evaluated for the presence of apical and coronal die leakage. The coronal leakage results are shown in FIG. 5. The apical leakage results are shown in FIG. 6. (In both figures, the ordinate is Mean Leakage in mm; and LC=lateral condensation [Group 1]; O=OBTURA II™ [Group 2]; SB=SYSTEM B™ [Group 3]; Th=THERMAFIL™ [Group 4]; I=INNOENDO™ [Group 5]; and Iexp=INNOENDO™ using inventive protocol [Group 6]. The same lower case letter in two different bars means no statistical difference in the mean leakage results between those two bars.)

In both cases, it can be seen that Group 6, i.e., the use of the INNOENDO™ obturator with the inventive protocol, provides the best results both in terms of coronal and apical leakage, even though the results are not statistically different from Group 5. The protocol associated with Group 5 involves the application of a two-part adhesive primer to the root canal prior to filling with the sealer. Accordingly, even compared to Group 5, Group 6 provides a benefit in terms of a more efficient protocol.

Example 5

Root Fracture Resistance Study

Root fracture resistance was assessed of root canals sealed with various commercial products as follows:
Group 1: THERMAFIL™ (Tulsa Dental)
(With Manufacturer Recommended Sealer)
Group 2: Heated gutta percha (Hybrid)
(SYSTEM B DOWNPACK™ apical third, OBTURA II™ backfill with AH26™ sealer)
Group 3: Standard gutta percha
(Lateral condensation, AH26™ sealer)
Group 4: ENDOREZ™ (Ultradent)
(Resin coated gutta percha, lateral condensation, ENDOREZ™ sealer)
Group 5: EPIPHANY™ (Pentron Technologies)
(RESILON™ points, lateral condensation, EPIPHANY™ adhesives and sealers)
Group 6: INNOENDO™ Obturators (Heraeus Kulzer)
(With INNOENDO™ adhesives and sealers)
Group 7: INNOENDO™ Obturators (Heraeus Kulzer)
(Using Inventive Protocol)

Figure 7:
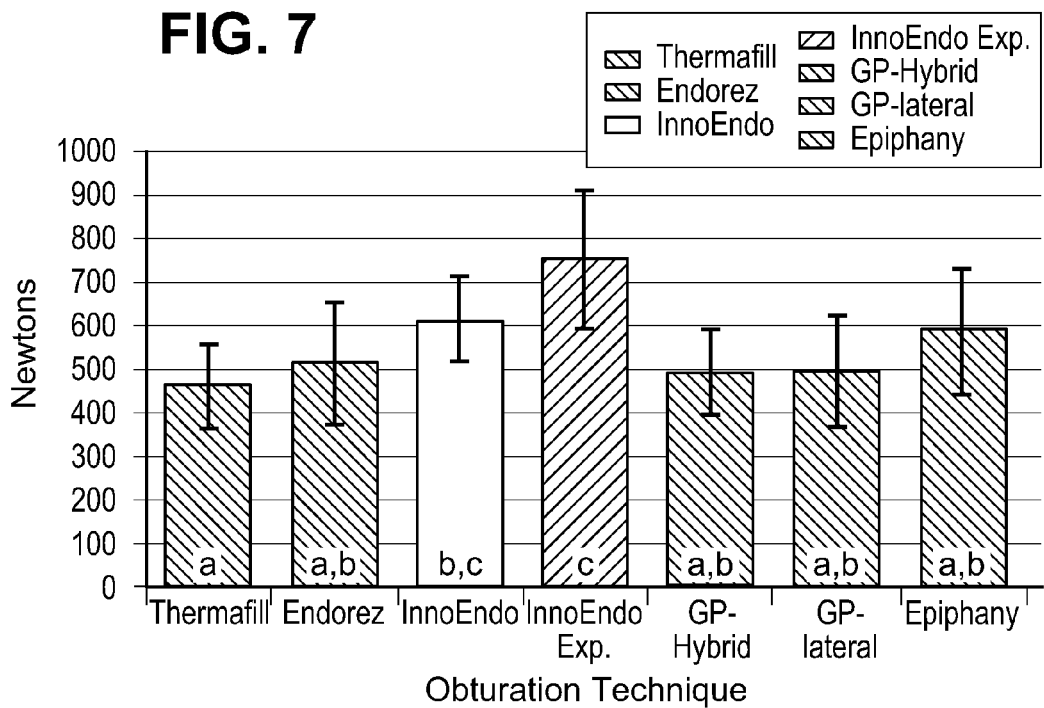
FIG. 7 is a chart comparing root fracture resistance results among various manufacturers/protocols.

The experimental protocol was as follows: Single canal extracted teeth sectioned of their clinical crowns were obturated according to the manufacturer's instructions for each group or in the case of Group 7 as described herein. The obturated teeth were then stored in 100% humidity for 48 hours at 37° C. to allow for complete setting of sealers. A vertical loading force was applied to the obturated roots with Model 4411 Instron at a crosshead speed of 1.0 mm/min. until the root fractured. The results are shown in FIG. 7.

It can be seen that Group 7, i.e., the inventive protocol (labeled "InnoEndo Exp." in FIG. 7,) exhibited the highest root fracture resistance of all of the groups tested, although again the results are not statistically different from Group 6. The protocol associated with Group 6 involves the application of a two-part adhesive primer to the root canal prior to filling with the sealer. Accordingly, even compared to Group 6, Group 7 provides a benefit in terms of a more efficient protocol.

Example 6

Figure 8:
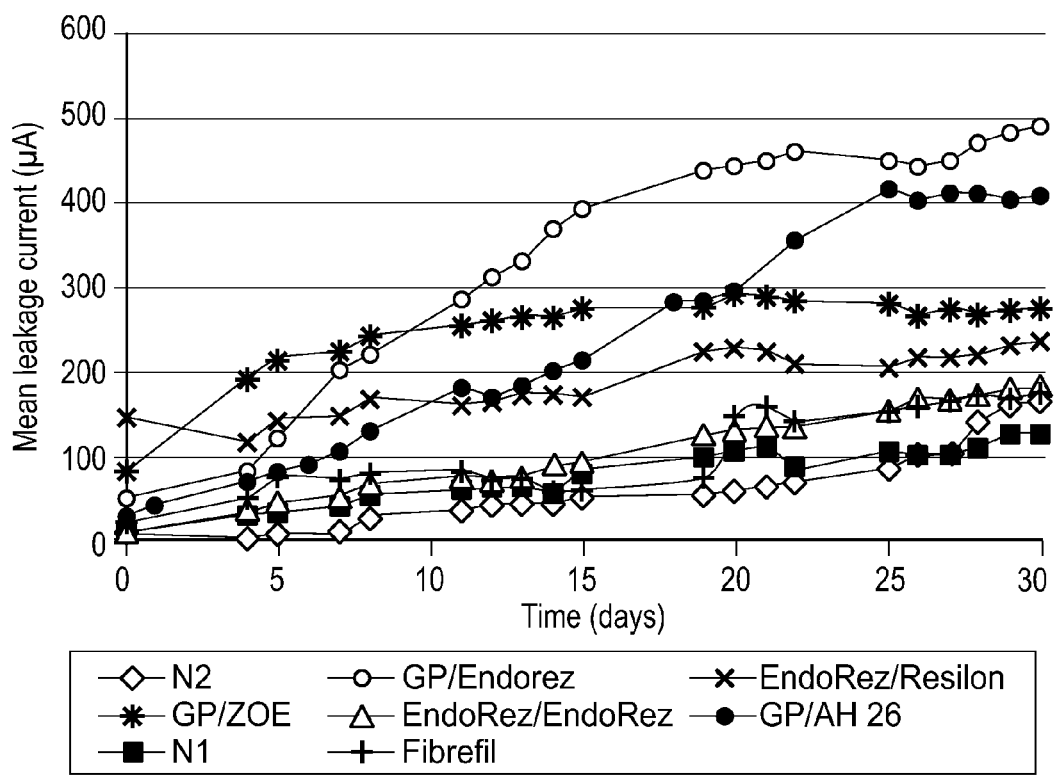
FIG. 8 is a chart comparing leakage resistance of various adhesive and non-adhesive obturators measured by electrophoresis method.

Leakage Resistance of Adhesive and Non-Adhesive Obturators by Electrophoresis Method Endodontic leakage resistance was assessed in root canals sealed with various adhesive based and non adhesive based obturators as follows:
Group 1: INNOENDO™ fiber obturator with INNOENDO™ adhesive and resin sealer
Group 2: INNOENDO™ fiber obturator with self-adhesive resin sealer
Group 3: FIBREFILL™ fiber obturator with FIBREFILL™ adhesive and resin sealer
Group 4: Gutta percha with ENDOREZ™ resin sealer
Group 5: ENDOREZ™ cone with ENDOREZ™ resin sealer
Group 6: RESILON™ cone with ENDOREZ™ resin sealer
Group 7: Gutta percha with ZOE™ sealer
Group 8: Gutta percha with AH26™ sealer The experimental protocol was as follows: Sixty-four human single rooted teeth, with 20 mm average working length, were used. Access was prepared coronally and patency confirmed with a hand file. The canals were instrumented to apical size ISO #40 with NaOCl irrigation, paper point dried, rinsed with 17% EDTA solution and re-dried before being randomly divided into eight groups of N=8. After preparation and obturation, a length of PVC-covered copper wire was placed coronally into each tooth in contact with the obturation material and sealed in place with sticky wax. Thereafter, the tooth/wax junction and all external surfaces of the teeth were sealed and insulated with 3 layers of nail varnish. Care was taken to ensure that the apices of the teeth remained patent. The teeth were immersed in 0.9% NaCl solution together with a stainless steel counter electrode. A 20V dc voltage was connected between the stainless steel and each tooth in turn, and current flow was determined by voltage drop across a standard resistor (100O) in the circuit. Current flow in the circuit was observed for 30 days. One way ANOVA with post hoc Scheffé testing at an apriori ∀=0.05. The results are shown in FIG. 8.

All specimens showed a progressive increase in leakage with time. Statistical analysis indicated that there were no differences ($p>0.05$) between the groups, primarily because of the large standard deviations within the sets of data. Nevertheless, the trends in behavior indicated that specimen leakage fell into two groups.

The greatest leakage was found in teeth obturated with gutta percha with ENDOREZ™ resin sealer and those obturated with gutta percha and AH26 sealer.

The least leakage was found with teeth obturated with INNOENDO™ fiber obturator and INNOENDO™ adhesive and resin sealer, an INNOENDO™ fiber obturator with a self-adhesive resin sealer, an ENDOREZ™ cone with ENDOREZ™ resin sealer and a FIBREFILL™ fiber obturator with FIBREFILL™ adhesive and resin sealer. Teeth obturated with gutta percha with ENDOREZ™ resin sealer and those obturated with a RESILON™ cone with ENDOREZ™ resin sealer were intermediate in behavior.

These findings indicate that the use of fiber obturators combined with newer adhesives holds great promise for achieving consistent leak-free root canal obturation.

It should be understood that the preceding detailed description of the invention is merely a detailed description of a small number of preferred embodiments of the present invention and that numerous changes to the disclosed embodiment(s) can be made in accordance with the disclosure herein without departing from the spirit or scope of the invention. The preceding detailed description of the invention, therefore, is not meant to limit the scope of the invention in any respect. Rather, the scope of the invention is to be determined only by the appended issued claims and their equivalents.

What is claimed is:

1. A method of filling and sealing a root canal during an endodontic procedure, said method comprising:
    a) filling said root canal with a combination consisting of:
        i) an obturator composed in a first part of fiberglass and in a second part of a chemically-bondable material; and
        ii) a self-etching adhesive or self-adhesive resin-based cement or sealer; and
    b) curing said combination to seal said root canal.

2. The method according to claim 1, wherein the chemically-bondable material is gutta percha treated in such a way as to render the gutta percha chemically bondable.

3. The method according to claim 1, wherein the chemically-bondable material is a polyester based thermoplastic material.

4. The method according to claim 1, wherein the chemically-bondable material is or contains a glass ionomer or resin-modified glass ionomer.

5. The method according to claim 1, wherein the root canal is filled with a combination consisting of the obturator and a self-adhesive cement.

6. The method according to claim 5, wherein the self-adhesive cement comprises a polymerizable composite material comprising at least one multifunctional acid containing monomer.

7. The method according to claim 1, wherein the root canal is filled with a self-adhesive sealer.

8. The method according to claim 1, wherein the combination is cured by light.

9. The method according to claim 1, wherein the combination is cured chemically.

10. The method according to claim 1, wherein the combination is cured both by light and chemically.

11. The method according to claim 1, wherein the self-etching adhesive or self-adhesive resin-based cement or sealer comprises acid-containing monomers.

12. The method of filling and sealing a root canal during an endodontic procedure according to claim 1, said method comprising:
   a) without previously separately applying adhesive primer to the walls of a root canal, filling said root canal with a combination consisting of:
      i) an obturator composed in a first part of fiberglass and in a second part of a chemically-bondable material; and
      ii) a self-etching adhesive or self-adhesive resin-based cement or sealer; and
   b) curing said combination to seal said root canal.

* * * * *